US00PP27619P2

(12) United States Plant Patent
Egger

(10) Patent No.: US PP27,619 P2
(45) Date of Patent: Jan. 24, 2017

(54) SEDUM PLANT NAMED 'DARK MAGIC'

(50) Latin Name: *Sedum telephium*
Varietal Denomination: Dark Magic

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 27 days.

(21) Appl. No.: 14/756,167

(22) Filed: Aug. 11, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

Declaration of Janet N. Egger dated Aug. 5, 2015.

*Primary Examiner* — Keith Robinson
(74) *Attorney, Agent, or Firm* — Klarquist Sparkman, LLP; Sheree Rybak

(57) ABSTRACT

A new and distinct hybrid of *Sedum* plant substantially as shown and described characterized by dark pink flowers in large inflorescences, glossy red black leaves in summer with serrate leaf margins, strongly upright stems, and a medium short, narrow clumping habit.

2 Drawing Sheets

Botanical denomination: *Sedum telephium.*
Variety designation: 'Dark Magic'.

BACKGROUND OF THE INVENTION

The present invention relates to a new and distinct cultivar of *Sedum* and given the cultivar name of 'Dark Magic'. *Sedum* is in the family Crassulaceae. *Sedum* 'Dark Magic' originated from an open pollinated cross from *Sedum* 410-3, an unnamed proprietary, unpatented *Sedum telephium* seedling. The new cultivar is planned as an accent for the landscape that is narrow and short with strong stems that stay very upright.

Compared to *Sedum telephium* 410-3, the seed parent, the new cultivar is shorter and narrower, with a better crown, and a larger inflorescence.

Compared to *Sedum* 'Raspberry Truffle' (U.S. Plant Pat. No. 22,755), cultivar is shorter, with a better crown, a darker, glossier leaves, and a larger, darker pink inflorescence.

Compared to *Sedum* 'Cherry Truffle' (U.S. Plant Pat. No. 24,602), cultivar is shorter and narrower in habit, with darker, glossier leaves, and a darker pink inflorescence.

This new and unique *Sedum* is distinguished by:

1. dark pink flowers in large inflorescences,
2. glossy, red black leaves in summer with serrate leaf margins,
3. strongly upright stems, and
4. a medium short, narrow clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one and a half-year-old *Sedum* 'Dark Magic' in bud growing in full sun in the trial bed outside in late July in Canby, Oreg.

FIG. 2 shows a one and a half-year-old 2 gallon plant in bloom in August.

DETAILED PLANT DESCRIPTION

Figure 3:
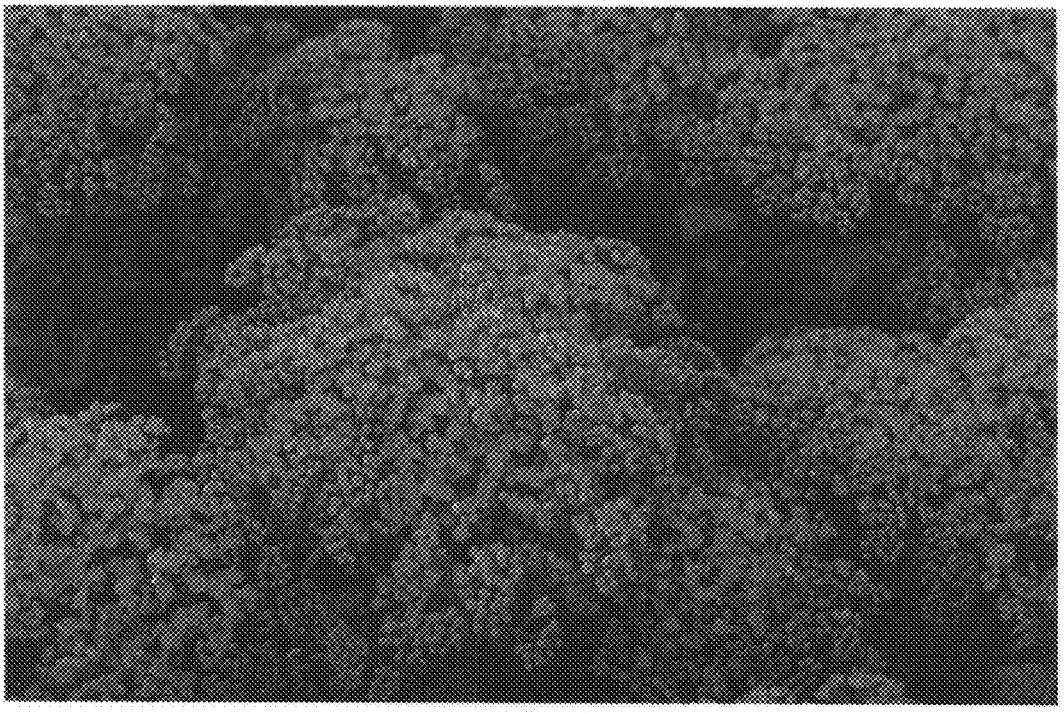
FIG. 3 shows a close-up of the flowers.

The following is a detailed description of the new *Sedum* hybrid based on observations of one and half-year-old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5$^{th}$ edition, 2007.

Plant:

*Type.*—Herbaceous perennial.
*Hardiness.*—USDA Zone 4 to 9.
*Size.*—38 cm tall from the ground to the top of the inflorescence and 50 cm wide.
*Habit.*—Erect, clumping.
*Vigor.*—Excellent.

Stem: Unbranched.

*Number.*—About 22.
*Size.*—33 cm long and 7 mm wide.
*Internode length.*—2 mm to 17 mm.

*Surface*.—Glabrous, glossy.
*Color*.—Greyed Purple 187A.

Leaf:
*Type*.—Simple.
*Arrangement*.—Alternate.
*Shape*.—Elliptic to oblong.
*Apex*.—Acute to obtuse.
*Base*.—Truncate to slightly cordate.
*Venation*.—Pinnate.
*Margins*.—Irregularly serrate.
*Blade size*.—Grows to 7 cm long and 3.3 cm wide.
*Surface*.—Glabrous on both sides.
*Texture*.—Thick, succulent.
*Petiole*.—Leaves sessile.
*Leaf color*.—Summer topside Greyed Purple N186B, including the vein, bottom side Green N137A heavily tinted Greyed Purple 187A, vein Greyed Purple 187A; spring topside Greyed Purple 187A, bottom side Green N137A lightly tinted Greyed Purple 187A, vein Greyed Purple 187A.

Inflorescence:
*Type*.—Terminal, corymbose, umbel-like.
*Number of flowers*.—About 1000 per stem.
*Peduncle*.—None.
*Rachis*.—About 5 cm long and 6 mm wide, Greyed Purple 187A, succulent, glabrous.
*Pedicels*.—3 mm to 4 mm long and 1 mm wide, glaucous, Brown N200B.
*Size*.—Grows to 11 cm deep and 18 cm wide.
*Bloom period*.—August through September in Canby, Oreg.

Flower bud:
*Size*.—2.5 mm wide, 3.5 mm deep.
*Description*.—Conical.
*Color*.—Greyed Purple 186C on top half and lightening to 186D on bottom.

Flower:
*Type*.—Complete, actinomorphic.
*Shape*.—Stellate.
*Size*.—6 mm deep and 11 mm wide.
*Color*.—Purple 76D.
*Corolla description*.—4 mm deep and 5.5 mm wide, 5 petals, each lanceolate, cupped, 5 mm long and 1.5 mm wide, margins entire, tip acuminate, base rounded, both sides glabrous and Red Purple 70B on top half and lightening to Red Purple 69C on bottom.
*Calyx description*.—1.5 mm deep and 2.5 mm wide, campanulate, 5 lobes, divided to the base, margins entire, tip acute, glabrous, Grey Brown N200A on both sides.
*Stamen description*.—8 in number, 3 mm long, filaments 3 mm long, Red Purple 65A, anthers Greyed Purple 186C, very little pollen, White 155A.
*Pistil description*.—4 to 5 separate prominent carpels, each 3 mm deep and 1.5 mm wide, Greyed Purple 186A on top half to Greyed Purple 186D on bottom half with stigma Greyed Purple 187A.
*Fragrance*.—None.
*Lastingness*.—Each stem lasts up to a month.

Fruit:
*Type*.—Ventrally dehiscent follicle, erect, attenuate.
*Fertility*.—None.
*Color*.—Brown 200A.

Seed: No seed produced.

Disease and pest tolerance: The new cultivar is typical to the genus. No known resistances to pests or diseases. No problems have been found in four years of growing in Canby, Oreg.

I claim:

1. A new and distinct hybrid of *Sedum* plant as herein illustrated and described.

* * * * *

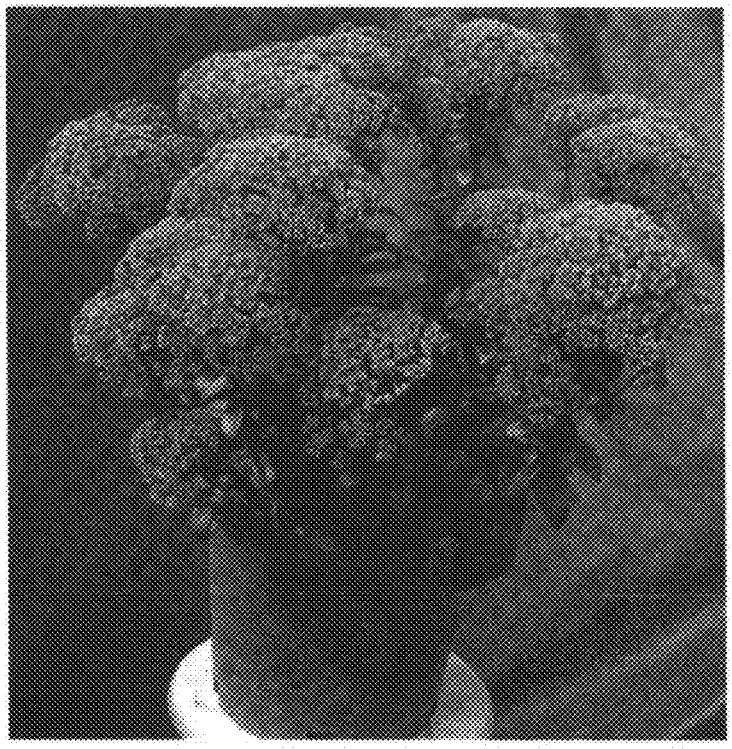

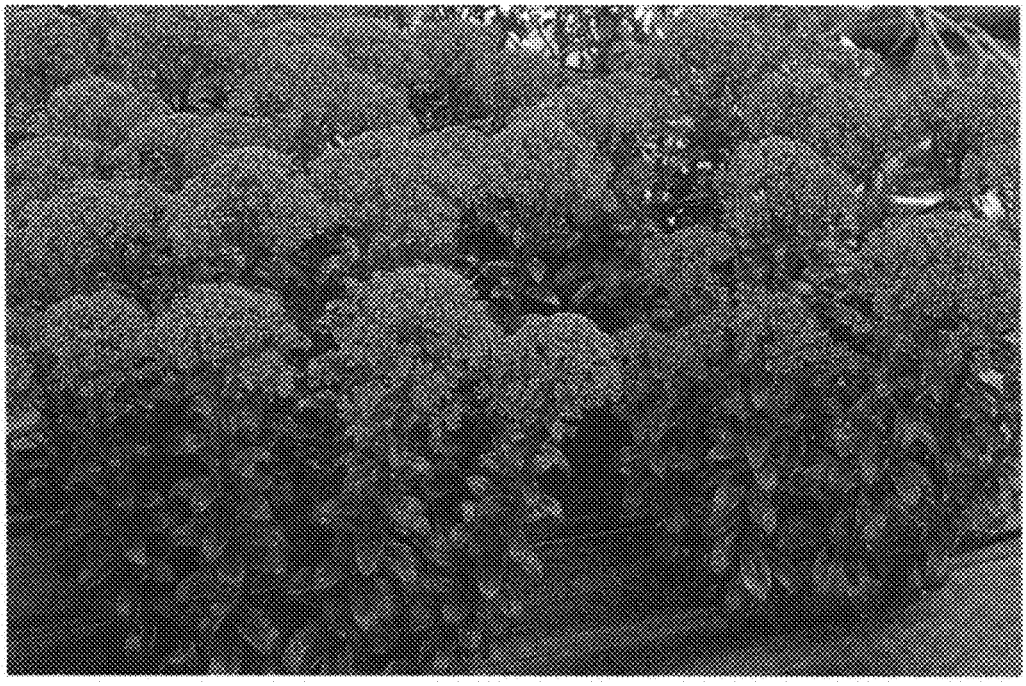
FIG. 1 above, FIG. 2 below